United States Patent
Lang

Patent Number: 5,109,471
Date of Patent: Apr. 28, 1992

[54] DEVICE FOR WARMING AND HUMIDIFYING GASES AND MORE PARTICULARLY RESPIRATORY GASES DURING ARTIFICIAL RESPIRATION

[76] Inventor: Volker Lang, Zugspitzstrasse 52, 8035 Gauting, Fed. Rep. of Germany

[21] Appl. No.: 557,511

[22] Filed: Jul. 24, 1990

[30] Foreign Application Priority Data

Jul. 24, 1989 [DE] Fed. Rep. of Germany ....... 3924456
Jan. 23, 1990 [DE] Fed. Rep. of Germany ....... 4001773

[51] Int. Cl.⁵ .......................... F24F 6/08; F24F 6/10; F22B 1/28
[52] U.S. Cl. ...................................... 392/396; 392/395
[58] Field of Search ............... 392/394, 395, 403, 405, 392/406, 396; 261/94, 99

[56] References Cited

U.S. PATENT DOCUMENTS

| | | | |
|---|---|---|---|
| 3,638,926 | 2/1972 | Melville | 392/395 |
| 3,659,604 | 5/1972 | Melville | 392/394 |
| 3,916,891 | 11/1975 | Freytag et al. | 128/192 |
| 3,982,095 | 9/1976 | Robinson | 392/395 |
| 4,048,993 | 9/1977 | Dobritz | 128/212 |
| 4,060,576 | 11/1977 | Grant | 392/594 |
| 4,529,867 | 7/1985 | Velnosky | 392/395 |
| 4,618,462 | 10/1986 | Fisher | 392/395 |

FOREIGN PATENT DOCUMENTS

| | | |
|---|---|---|
| 2236519 | 2/1975 | France . |
| 2315955 | 1/1977 | France . |
| 2001248 | 1/1979 | United Kingdom . |
| 2053695 | 2/1981 | United Kingdom . |

*Primary Examiner*—Teresa J. Walberg

[57] ABSTRACT

An apparatus for warming and humidifying respiratory gases during artificial respiration includes two passive heat and moisture exchangers and an active warming and humidifying element disposed between them in a housing. The first passive heat and moisture exchanger serves to preheat and prehumidify cold and dry gases to be inhaled. In a further, downstream, active heat and moisture exchanger and the second heat and moisture exchanger, gases are additionally heated and humidified, thus ensuring optimum physiological conditioning of the respiratory gases to a temperature of 36°-37° C and 100% relative humidity. In an exhalation phase, 70 to 80% of humidity and heat are recovered from the optimally conditioned humid and warmed respiratory gas with the aid of the two integral passive heat and moisture exchangers.

17 Claims, 2 Drawing Sheets

DEVICE FOR WARMING AND HUMIDIFYING GASES AND MORE PARTICULARLY RESPIRATORY GASES DURING ARTIFICIAL RESPIRATION

The invention relates to a device for warming and humidifying gases and more particularly for respiratory gases during artificial respiration.

BACKGROUND OF THE INVENTION

Under physiological conditions the nose serves to actively warm up and humidify respiratory air. However, when a patient is undergoing artificial respiration, the nose is shunted by a tube or piece of hose which has one end lodged in the trachea. Thus, in such a situation the nose cannot accomplish the usual warming and humidifying functions that it normally achieves. Therefore, in such situations artificial humidification and warming of the air, which are absolutely essential for proper pulmonary function, are presently accomplished by devices based on two different principles.

Apparatus of a first type actively transfers heat and moisture to the respiratory air. The apparatus of the first type, for example, the dry, cold respiratory air is passed through an electrically heated water bath humidifier and conditioned prior to being supplied to a patient. A second type of apparatus operates passively as a heat and moisture exchanger (H.M.E.), in which case the heat and moisture are extracted from moist exhaled air at body temperature and are transferred to cold, dry air to be inhaled by a patient without actively supplying heat and moisture from the outside, that is from an external source thereof.

While it is true that state-of-the-art apparatus operating on the principle of actively supplying heat and moisture to the air is able to supply respiratory gases in a well tempered and satisfactorily humidified form, this is achieved at the expense of substantial technical complexity and requires considerable nursing attention. Consequently, the purchase price and operating costs of such apparatus are very high. On the other hand, with simple passive heat and moisture exchangers, which are of simple design and are simple to use, no such expenses are involved, although such second type of apparatus has thus far not performed satisfactorily to humidify and warm up respiratory air during artificial respiration.

There exists, therefore, the need for such a device which can perform satisfactorily and which at the same time, does not exhibit the technical complexity or require the nursing attention of state-of-the-art apparatus. The present invention fulfills such a need.

BRIEF STATEMENT OF THE INVENTION

Accordingly it is an object of the present invention to provide an apparatus to humidify and warm up respiratory air during artificial respiration which is of the simplest possible structure in order to simplify the operation thereof.

In order to achieve these or other objects which are apparent from the instant application, apparatus according to the invention comprises in combination at least one passive heat and moisture exchanger and at least one active warming and humidifying device. Thus, advantages of both principles are united in a single device on apparatus so that on the one hand there is optimum humidification and warming up of the respiratory gases while at the same time the apparatus involves only minor technical complexity, minimum nursing attention and expense.

One advantageous feature of the inventive apparatus or device is that it may be arranged in a housing, for example, in the form of a plurality of cells, in which arrangement there is first a passive heat and moisture exchanger disposed upstream in the direction of flow of the gas to be humidified, following which an active warming and humidifying device consisting of at least one heating device, a water supplying device and a suction layer is disposed. The suction layer is located following the water supplying device and the active warming and humidifying device itself is followed by a passive warming and humidifying device or heat and moisture exchanger.

THE DRAWINGS

In order to understand the present invention more fully, reference is directed to the accompanying drawings which are to be taken in conjunction with the following detailed description of the invention and in which drawings:

FIG. 1 is a perspective, exploded view, partially in section, of a three-part working example of a device or apparatus according to the invention; and FIG. 2 is a sectional view taken on line II—II of the device or apparatus illustrated in FIG. 1 in assembled condition.

DESCRIPTION OF THE PREFERRED EMBODIMENTS

Figure 1:
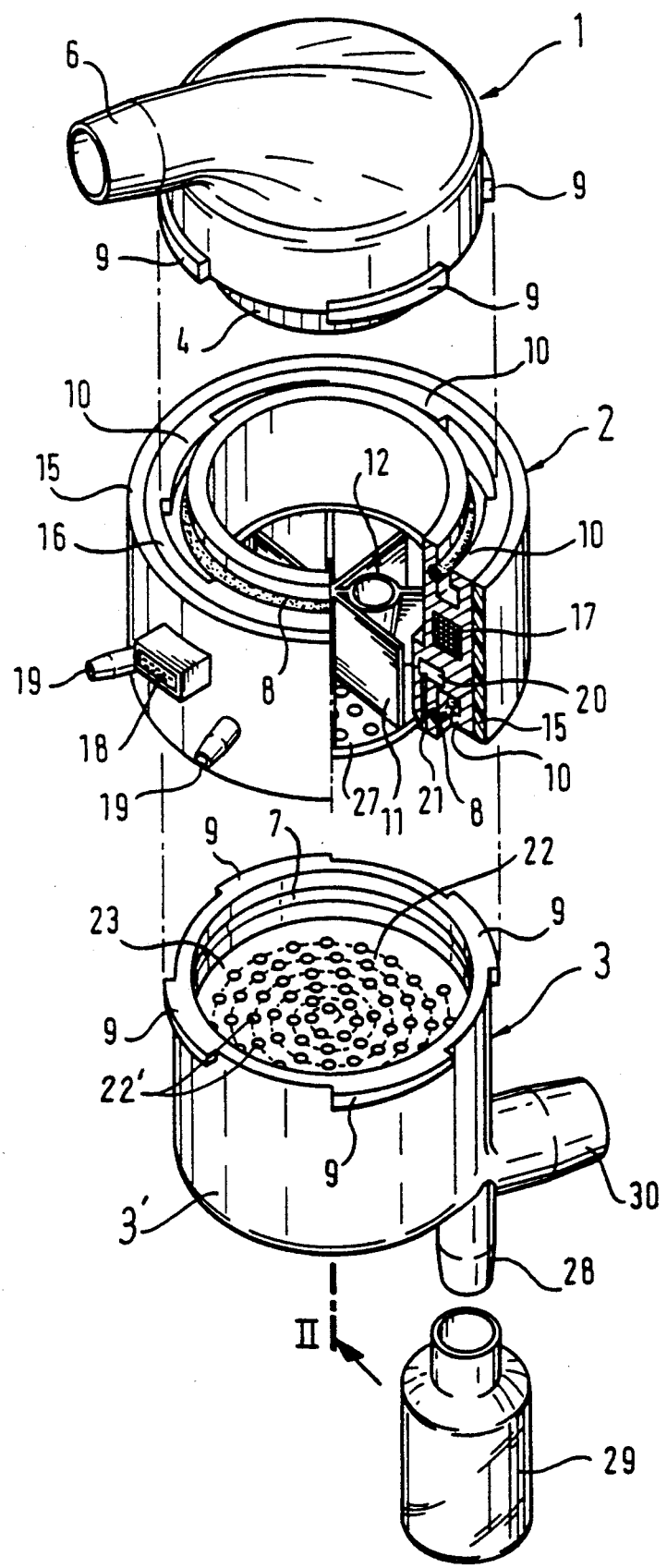
Figure 2:
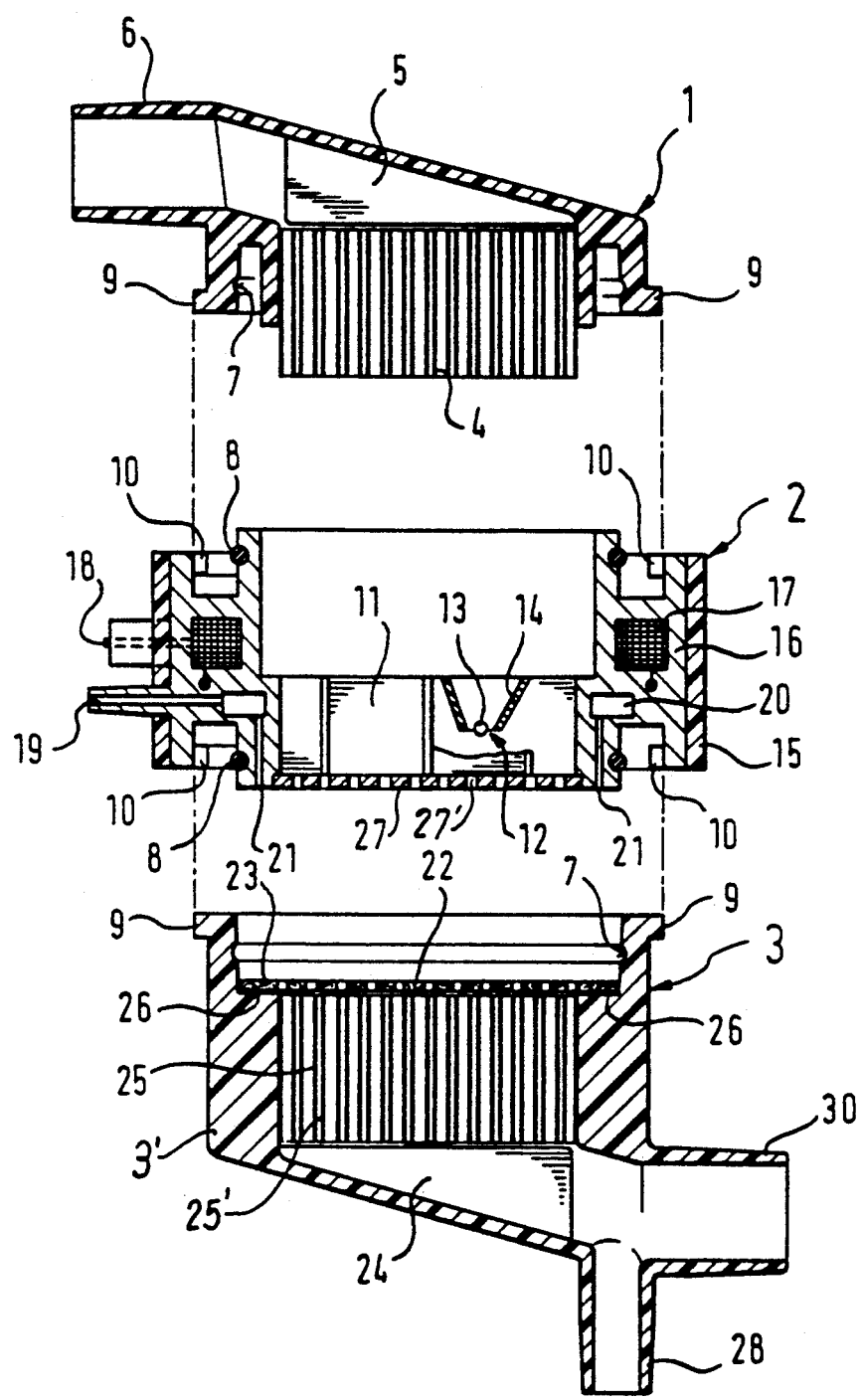

Referring now more particularly to FIGS. 1 and 2, a device or apparatus in accordance with the invention comprises a hood 1 in the form of a squat plastic hollow cylinder which has a standard respiratory gas hose connector 6 joined to it and which is adapted to offer a minimum resistance to flow. Hood 1 contains a first passive heat and moisture exchanger 4 (FIG. 2) which is arranged so that it is held against the domed housing cover or hood by a thin-walled support rib 5. Gas entering via the standard respiratory air connector 6 is able to pass freely through the numerous air ducts, opening in the surface of the passive heat and moisture exchanger 4, into center element 2. The passive heat and moisture exchanger may be in the form, for example, of an insert cartridge, such as those distributed by Swedish company Gibeck Respiration A.B. Center element 2 simultaneously serves as a mechanical connecting member between hood 1 and a bottom element 3. The connection is achieved by a detent, sealing and clamping elements, as, for example, detent grooves 7, detent beads 8 and, respectively, O-rings 10 or bayonet locking elements 9.

Within center element 2 there are supporting and heating ribs 11 and a flow meter or flow sensor 12. The flow meter or flow sensor 12 consists of an input funnel 14 having a heated PTC resistor 13 located in the lumen or bore, as shown in FIG. 2. The PTC resistor 13 is connected in any convenient manner through detecting means (not shown) of a known type to an external controller (not shown) of a known type to deliver distilled or sterile water to element 2 in a precisely metered manner. In addition, it is connected in any convenient manner through detecting means of a known type to a source of electrical energy through the external controller and, as well, is connected to an artificial respiration apparatus (not shown) by detecting means (not shown) to detect respiratory motion or strokes of the artificial respiratory apparatus and thus permit the supply of water and electrical energy to take place as needed upon detection of such respiratory motion or strokes of the artificial respiratory apparatus. For thermal insulation of the center element 2, which is provided with metallic casing 16, there is an external plastic casing 15. For thermostatically controlled heating of the distilled sterile water, which is supplied from a source (not shown) via a connector 19 into an annular duct 20 in a precisely metered manner by an external controller (not shown) of a known type, a heating device provided with two NTC resistors such as NTC resistor 17 is disposed in center element 2. This heating device is also connected with the external controller, which may be of a known type, as previously mentioned, via its own electrical wiring 18. The water is supplied from this annular channel 20 via a plurality of nozzles 21 to the marginal zone 23 of a thick absorbent paperboard disk 22 provided with spiral holes 22', or a metal frit structure having coarse pores, like a sieve, which forms a suction layer. The water is evenly distributed in this disk or suction layer by capillary forces.

Since the absorbent layer, that is to say the special purpose paperboard disk 22, not only bears on the passive heat and moisture exchanger 25 which is located in a bottom element 3 comprising a plastic housing 3', and is supported and protected by a thin-walled holding rib 24 located in the housing, but in addition, has its edge 23 welded on the lower side 26 to the plastic housing and is pressed against the same by a metal disk 27, or a metal grid, which is precisely tempered and supported in the center element 2 and is provided with the perforations or holes 22', like a sieve. After saturation of the suction layer 22 with water, there is an even and active humidification and warming action in the passive heat and moisture exchanger 25. Excess water applied to this second passive heat and moisture exchanger 25 drips off under the effects of gravity through the ducts 25' located therein and reaches the sloping bottom of element 3, where it flows into connector 28 arranged at the lowest point thereof. A small transparent collecting container 29, which may also be in the form of a water trap, is slipped on to connector 28. Thus, it is not possible for excess water on the passive heat and moisture exchanger 25 to pass into the respiratory hose connector 30 and thence via an adjoining adapter part (not shown) for connection to the tracheal tube, into the lungs of the patient undergoing artificial respiration.

A detailed description of the operation of device of this invention is now set forth with reference to the above-described embodiment thereof.

Dry, cold respiratory gas (at about 20° C. with 10-20% relative humidity) passes during the inhalation phase from an artificial respiration machine (not shown) via the patient-hose connector system to the respiratory gas hose connector 6 of the hood 1, whence the respiratory gas flows through the first heat and moisture exchanger 4 installed at this point and in a first stage it is preheated and prehumidified by stored heat and moisture passively, such stored heat and moisture previously having being transferred from the exhaled air (at body temperature) from the patient undergoing artificial respiration. This respiratory gas then, however, only reaches a temperature of about 30° C. and a relative humidity of about 100%. These temperature and humidity values are, however, insufficient.

In a second stage, the active humidifying and warming stage, the center element 2, that is the active warming and humidifying device (which is supplied via an external controller with precisely metered water and electrical heating energy) causes the respiratory gas flowing therethrough to be additionally heated and humidified using heating ribs 11. Warmed water then flows from the heated annular duct 20 and the adjoining nozzles 21 through the heated metal plate 27 with sieve perforations 27' therein and into the thick absorbent special purpose paperboard disk 22 or suction layer provided with sieve perforations 22', wherein the water is evenly distributed by capillary forces. From the special purpose paperboard disk 22 or suction layer, the water spreads out evenly in the plurality of ducts 25' in the second passive heat and moisture exchanger 25, whose surface area is very large due to the large number of ducts. This subsequent heating and subsequent humidification enables the respiratory gas to reach temperatures of 36°-37° C., 100% relative humidity without any difficulty even when large volumes of air are being inhaled.

During the exhalation phase the humid respiratory gas at body temperature (36°-37° C., 100% relative humidity) flows in a reverse direction out through the connector 30, through the second passive heat and moisture exchanger 25 and then via element 2 to and through the first passive heat and moisture exchanger 4 and surrenders at least 70-80 % of its moisture and heat, the greater part of such heat and humidity being transferred to the first passive heat and moisture exchanger. The result of this is that there is only a small accumulation of condensate in the exhalation hose. There is thus the additional advantage over conventional systems of less nursing attention being required, as well as better bacteriological hygiene.

Since in the device in accordance with the invention the technically most complex part, namely the center element 2, may be produced in form of a connecting member which is simple to clean and which is able to be sterilized with steam, it may be re-used. One the other hand, the two heat and moisture exchangers 4 and 25, may be produced in a sterile state cheaply for a single use only with the plastic housings 1 and 3. This means that there will not only be optimum conditioning and tempering, but furthermore, protection against infection. Thus, the device is also economical.

Due to the incorporation of the flow sensor 12, which permits the supply of water and electrical energy to take place from the external controller when respiratory motion or strokes of the artificial breathing machine are detected, that is to say when there is a rhythmic cooling of the PTC resistor, there results a further contribution towards patient safety when using the inventive device, since even in the case of extreme conditions of operation it precludes the chances of hot respiratory gases or water passing into the trachea of the patient.

What is claimed is:

1. An apparatus for warming and humidifying respiratory gases comprising in combination at least one passive heat and moisture exchanger and at least one active warming and humidifying element, said at least one active element including heat generating means, said exchanger and said element being disposed in a housing with said exchanger being located upstream in the direction of flow of said respiratory gases to be warmed and humidified with respect to the disposition of said element.

2. An apparatus according to claim 1 including a flow sensor located in the active warming and humidifying element as an integral part thereof, said flow sensor being capable of detecting the volumetric respiratory gas flow through said element and activating said element.

3. An apparatus according to claim 2 wherein the flow sensor is an intake funnel having a PTC resistor disposed in the lumen thereof.

4. An apparatus according to claim 1 wherein the housing is a two part housing, one part of said housing containing the passive heat and moisture exchanger and the other part of said housing containing the active warming and humidifying element.

5. An apparatus according to claim 1 wherein the active warming and humidifying element comprises at least one water supplying means, an absorbent layer and a heating means.

6. An apparatus according to claim 1 including an additional passive heat and moisture exchanger located in the housing downstream from the active warming and humidifying element.

7. An apparatus according to claim 6 including a housing which is divided into three parts, the first part of said housing containing the passive heat and moisture exchanger located upstream in the direction of flow of the respiratory gases, the second part of said housing containing the active warming and humidifying element and the third part of said housing containing the additional passive heat and moisture exchanger located downstream from the active warming and humidifying element.

8. An apparatus according to claim 6 wherein the housing is divided into three parts, the first part of said housing being a hood having a connector attached thereto and containing the first passive heat and moisture exchanger, the second part of said housing containing the active warming and humidifying element which has connections attached thereto for supplying distilled water and heat to said element, the third part of said housing containing the second passive heat and moisture exchanger and an absorbent layer disposed between said active warming and humidifying element and said second passive heat and moisture exchanger.

9. An apparatus according to claim 8 wherein the third part of the housing slopes downwardly at the low end thereof and includes a collecting container attached thereto through a collecting connector.

10. An apparatus according to claim 8 wherein the first and third parts of the housing are made of plastic and together with the passive heat and moisture exchangers contained therein and the absorbent layer disposed between the active warming and humidifying element and the second passive heat and moisture exchanger form sterilizable units.

11. An apparatus according to claim 8 wherein the active warming and humidifying element is made of metal and includes connecting means for attaching said element with cooperating connecting means on the first and third parts of the housing.

12. An apparatus according to claim 11 wherein the active warming and humidifying element is coated with a thermally insulating plastic material.

13. An apparatus according to claim 8 wherein the active warming and humidifying element includes a plurality of water ducts and a thermostat for heating water from an external source to a constant temperature and which is supplied through said ducts to warm respiratory gases, humidifying liquid and the second heat and moisture exchanger disposed in the third part of the housing.

14. An apparatus according to claim 8 wherein the active warming and humidifying element includes a tempered metal disk provided with a plurality of sieve-like openings which is disposed over the absorbent layer and said absorbent layer is a thick paperboard disk provided with a plurality of sieve-like openings, said metal disk pressing said paperboard disk with gentle force against the second passive heat and moisture exchanger, and said metal disk and said paperboard disk together forming a heat and moisture distributor.

15. An apparatus according to claim 8 wherein the active warming and humidifying element includes a tempered metal grid which is disposed over the absorbent layer and said absorbent layer is a thick paperboard disk provided with a plurality of sieve-like openings, said metal grid pressing said paperboard disk with gentle force against the second passive heat and moisture exchanger, and said metal grid and said paperboard disk together forming a heat and moisture distributor.

16. An apparatus according to claim 8 wherein the active warming and humidifying element includes a tempered metal disk provided with a plurality of sieve-like openings which is disposed over the absorbent layer and said absorbent layer is a metal frit disk provided with a plurality of coarse pores, said metal disk pressing said metal frit disk with gentle force against the second passive heat and moisture exchanger, and said metal disk and said metal frit disk together forming a heat and moisture distributor.

17. An apparatus according to claim 8 wherein the active warming and humidifying element includes a tempered metal grid which is disposed over the absorbent layer and said absorbent layer is a metal frit disk provided with a plurality of coarse pores, said metal grid pressing said metal frit disk with gentle force against the second passive heat and moisture exchanger, and said metal grid and said metal frit disk together forming a heat and moisture distributor.

* * * * *